United States Patent [19]

Gordon

[11] 4,237,557
[45] Dec. 9, 1980

[54] CONTROL SYSTEM FOR WELDING HELMET LIQUID CRYSTAL LIGHT SHUTTER

[76] Inventor: Mack Gordon, 1724 Wilbur Rd., Medina, Ohio 44256

[21] Appl. No.: 62,195

[22] Filed: Jul. 30, 1979

[51] Int. Cl.³ .............................................. A61F 9/06
[52] U.S. Cl. .......................................... 2/8; 350/332
[58] Field of Search ................ 2/8; 219/147; 350/331, 350/332, 150

[56] References Cited
U.S. PATENT DOCUMENTS

| | | | |
|---|---|---|---|
| 3,821,765 | 6/1974 | Wagner et al. .................. | 350/331 X |
| 4,039,803 | 8/1977 | Harsch ..................................... | 2/8 X |

*Primary Examiner*—Peter P. Nerbun
*Attorney, Agent, or Firm*—Thomas H. Murray

[57] ABSTRACT

A control system and method for operating a welding helmet liquid crystal light shutter wherein opening of the liquid crystal light shutter is delayed by two or three seconds after a welding arc is extinguished to permit the welder to apply a welding electrode to the workpiece after the aforesaid two or three seconds to reheat a rapidly-cooling bead. The invention is particularly adapted for use in welding aluminum wherein it is a common practice to place a short weld at the end of a weld head to prevent rapid chilling of the head. In another embodiment of the invention, a liquid crystal light shutter for a welding helmet is caused to open or become transparent quickly; is held open for a few seconds; and is then closed for a few seconds during which latter time the auxiliary welding bead is applied to prevent rapid chilling.

3 Claims, 3 Drawing Figures

CONTROL SYSTEM FOR WELDING HELMET LIQUID CRYSTAL LIGHT SHUTTER

BACKGROUND OF THE INVENTION

While not limited thereto, the present invention is particularly adapted for use in liquid crystal welding helmet lens assemblies such as those shown in U.S. Pat. Nos. 4,039,254 and 4,039,803. Such a protective welding lens assembly comprises a layer of nematic liquid crystal material sandwiched between opposing parallel plates coated with transparent conductive films. The faces of the plates in contact with the liquid crystal material are treated so as to effect a twisted nematic structure therein which will rotate polarized light passing through the light shutter through 90°. Polarizers are disposed on opposite sides of the plates such that by applying an electrical field across the transparent conductive films, the opacity of the liquid crystal light shutter can be changed.

It is preferable in a welding helmet lens assembly to utilize parallel polarizers on opposite sides of the liquid crystal cell such that, when no electric field is applied across the transparent conductive films, polarized light cannot pass through the cell. That is, in order to render the cell light-transmitting, an electric field must be established across the conductive films. Among other things, this is for the reason that in the event of power failure, the cell will automatically assume an opaque condition and protect the eyes of the welder.

During a welding operation, the welding arc is sensed by a phototransistor or other wave energy sensing device which, through suitable circuitry, removes the electric field across the liquid crystal layer, thereby causing the cell to become opaque. It is, of course, highly desirable to switch from the light-transmitting to the opaque condition as quickly as possible. Nevertheless, because of the speed of operation of liquid crystal light shutters of this type, the welder will observe a momentary flash during the time the cell is changing from a light-transmitting to an opaque condition upon the establishment of a welding arc.

The momentary flash which the welder observes when an arc is initially struck presents special problems in the cause of aluminum welding. Electric welding of aluminum requires techniques different than those for conventional steels. That is, aluminum conducts heat very rapidly; and the weld bead head cools quickly when the electrode is removed from the work. As a result, rapid cooling results in weak welds. In order to overcome this condition, it is common practice to place a short weld at the end of the weld head two or three seconds after welding the main head. This slows chilling of the head and produces high quality welds. Because of the speed of operation of the liquid crystal light shutter as explained above, a welder working with aluminum will receive a momentary flash of light when he applies the welding electrode after two or three seconds to reheat the rapidly-cooling bead; and it is, of course, desirable to eliminate this condition.

SUMMARY OF THE INVENTION

In accordance with the present invention, the momentary flash which is observed when a short weld is placed at the end of a main aluminum weld head is eliminated. In one embodiment of the invention, this is accomplished by delaying the opening of the liquid crystal light shutter by two or three seconds after the arc is extinguished, whereby when the welder applies the welding electrode to the workpiece after two or three seconds to reheat the rapidly-cooling bead, he will not observe a momentary flash of light.

In another embodiment of the invention, the liquid crystal light shutter opens or becomes transparent quickly and is then held open for a few seconds and then closes for a few seconds, during which latter time the auxiliary welding bead is applied to prevent rapid chilling as explained above.

The above and other objects and features of the invention will become apparent from the following detailed description taken in connection with the accompanying drawings which form a part of this specification, and in which.

Figure 1:
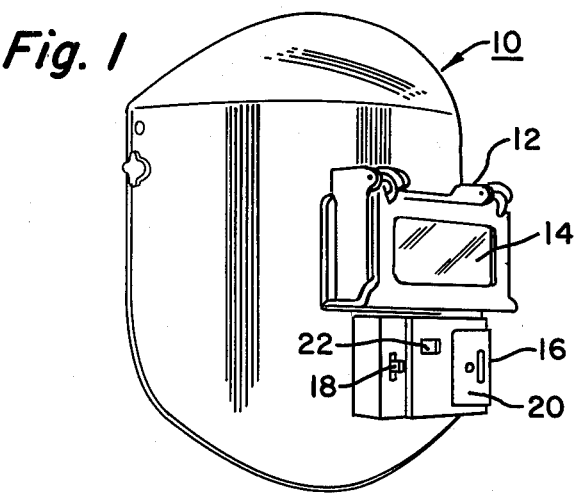
FIG. 1 is a perspective view of a welding helmet incorporating a liquid crystal light shutter assembly.

With reference now to the drawings, and particularly to FIG. 1, a welder's helmet 10 is shown provided with a window or lens assembly 12 having an eyepiece 14 comprising a liquid crystal light shutter hereinafter described in greater detail. Beneath the lens assembly 12 is an electronic unit 16 incorporating a manually-operated switch 18 which acts to switch the control system ON or OFF. Preferably, when the control system is switched ON by the switch 18, the liquid crystal light shutter 14 will change from a substantially opaque condition to a light-transmitting condition such that the welder can see through the light shutter under ambient light conditions. However, should there be a power failure or failure of the electronic circuitry itself, the liquid crystal light shutter 14 will automatically become opaque, thereby protecting the welder's eyes against a possible malfunction of the circuitry or a power failure.

The electronic unit 16 is provided with a door or flap 20 which can be opened to insert a battery into the unit. The unit is also provided with a window 22 behind which is a phototransistor.

Figure 2:
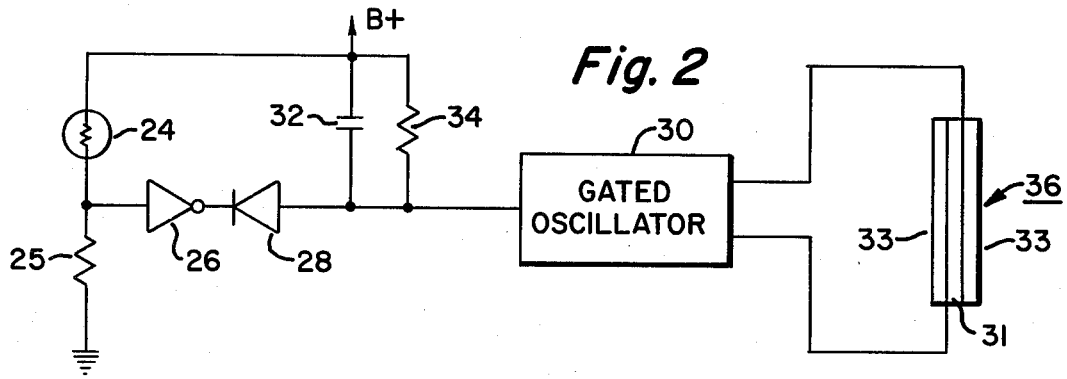
FIG. 2 is an illustration of one embodiment of the invention wherein opening of the light shutter is delayed after a welding arc is extinguished.

The phototransistor behind the window 22 is identified by the reference numeral 24 in FIG. 2. It is connected to ground through resistor 25 and to a source of positive potential, substantially as shown. One terminal of the phototransistor 24 is connected through an inverter 26 and a diode 28 to a gated oscillator 30. Connected between the B+ voltage source and the input to the gated oscillator 30 is an RC network consisting of capacitor 32 in shunt with resistor 34. The arrangement is such that when a welding arc is extinguished, this condition is sensed by the photocell 24; however the signal input to the oscillator 30 will not change for a period of 1 to 2 seconds while capacitor 32 discharges through resistor 34, which is sufficient to permit the welder, who is welding aluminum, to place a short weld at the end of the main weld head before oscillator 30 is turned ON to open the liquid crystal cell 36. Cell 36 comprises a layer 31 of nematic liquid crystal material sandwiched between glass plates 33 treated on their facing surfaces with transparent conductive films which are rubbed at right angles to achieve a twisted nematic structure. The cell is completed by parallel polarizers, not shown, on its two opposite sides.

Figure 3:
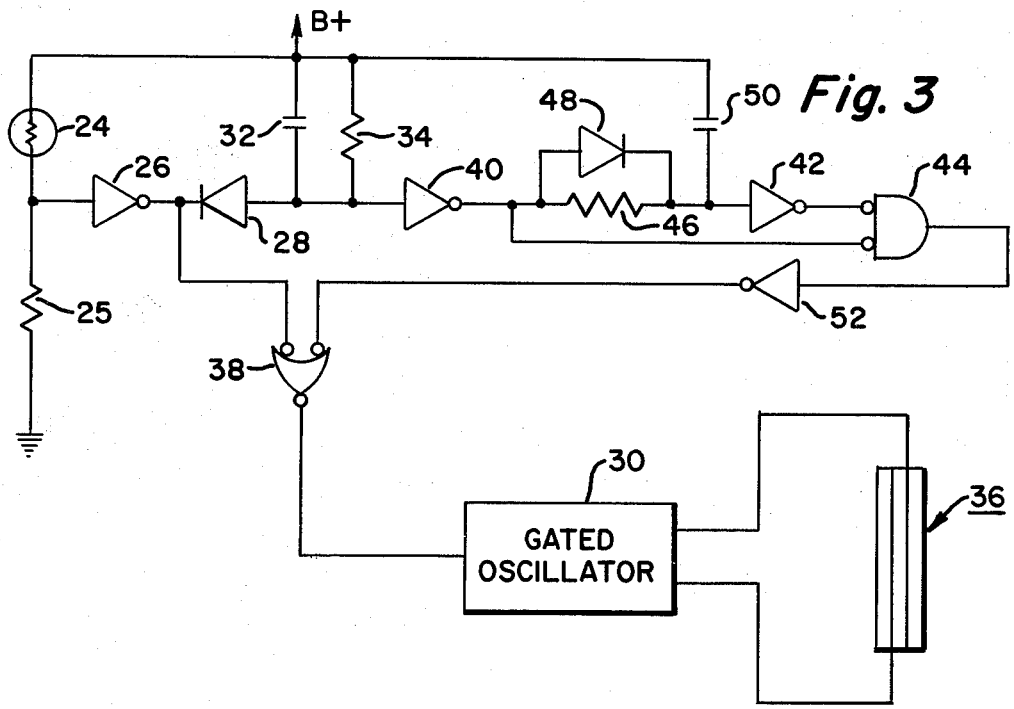
FIG. 3 is an illustration of another embodiment of the invention wherein the liquid crystal light shutter opens after a welding arc is extinguished, is held open for a few seconds, and then is closed for a few seconds.

In FIG. 3, another embodiment of the invention is shown wherein elements corresponding to those of FIG. 2 are identified by like reference numerals. In this case, however, the output of the inverter 26 is applied through OR gate 38 directly to the gated oscillator 30 such that the liquid crystal light shutter 36 will open as soon as the welding arc is extinguished at the end of the main weld. A delayed signal, produced by the RC network 32, 34, is applied through inverters 40 and 42 to one input of NOR circuit 44. The other input to the NOR circuit 44 is the output of the inverter 40, the two inverters 40 and 42 being interconnected by resistor 46 in shunt with a diode 48. Additionally, capacitor 50, which forms part of the RC network along with elements 32 and 34, connects the B+ voltage source to the input of inverter 42. The output of NOR circuit 44, in turn, is connected through inverter 52 to the other input of OR circuit 38.

With the arrangement shown, the oscillator 30 will be triggered into conduction whenever the welding arc is extinguished and thereafter will be disabled such that the shutter will become opaque for a predetermined period of time, on the order of about 1 to 2 seconds, to permit the welder to strike an arc at the end of the main weld bead.

Although the invention has been shown in connection with certain specific embodiments, it will be readily apparent to those skilled in the art that various changes in form and arrangement of parts may be made to suit requirements without departing from the spirit and scope of the invention.

What is claimed is:

1. A method for controlling a liquid crystal light shutter welding helmet lens assembly which comprises causing said shutter to approach an opaque condition whenever a welding arc is struck, and delaying an increase in the light transmission characteristics of said shutter after said arc is extinguished and until the welder has had an opportunity to again strike the arc momentarily.

2. A method for controlling a liquid crystal light shutter welding helmet lens assembly which comprises causing said shutter to approach an opaque condition whenever a welding arc is struck, causing said light shutter to increase its light transmission characteristics for a fixed period of time immediately after the welding arc is extinguished, and thereafter automatically increasing the opacity of said light shutter for a predetermined period of time whether or not a welding arc exists.

3. The method of claim 1 wherein the light transmission characteristics of said shutter are delayed after the arc is extinguished for a period of about 1 to 2 seconds.

* * * * *